(12) United States Patent
Richard-Bey

(10) Patent No.: US 7,350,520 B1
(45) Date of Patent: Apr. 1, 2008

(54) NEBULIZER DELIVERY DEVICE

(76) Inventor: Linda C Richard-Bey, 8321 S. King Dr., apt 1A, Chicago, IL (US) 60619

( * ) Notice: Subject to any disclaimer, the term of this patent is extended or adjusted under 35 U.S.C. 154(b) by 511 days.

(21) Appl. No.: 11/004,727

(22) Filed: Dec. 3, 2004

(51) Int. Cl.
*A61M 16/00* (2006.01)

(52) U.S. Cl. .......................... 128/200.21; 128/200.14; 128/203.12

(58) Field of Classification Search .......... 128/200.14, 128/200.21, 200.11, 200.24, 203.28, 204.18, 128/200.22, 203.12, 205.22; 222/78, 180, 222/181, 185, 192, 568; 446/61, 62, 93, 446/231, 71–78, 432; 248/206.2, 206.3; D24/110; 206/457

See application file for complete search history.

(56) References Cited

U.S. PATENT DOCUMENTS

| 165,799 | A | | 7/1875 | Daniels |
| 1,263,079 | A | | 4/1918 | Leon |
| 2,731,765 | A | * | 1/1956 | Carver ........................ 446/409 |
| 4,119,096 | A | | 10/1978 | Drews |
| 4,257,415 | A | * | 3/1981 | Rubin .................... 128/200.21 |
| 4,291,688 | A | | 9/1981 | Kistler |
| 4,685,456 | A | * | 8/1987 | Smart ..................... 128/205.22 |
| 4,773,410 | A | * | 9/1988 | Blackmer et al. ....... 128/203.26 |
| 4,823,784 | A | * | 4/1989 | Bordoni et al. ......... 128/200.14 |
| 5,312,281 | A | | 5/1994 | Takahashi et al. |
| 5,357,945 | A | * | 10/1994 | Messina ................. 128/200.14 |
| 5,474,486 | A | * | 12/1995 | Chilton et al. .............. 446/456 |
| D383,838 | S | * | 9/1997 | Solano ....................... D24/110 |
| 5,690,096 | A | * | 11/1997 | Burch ..................... 128/204.18 |
| 5,704,344 | A | * | 1/1998 | Cole ....................... 128/200.14 |
| D397,785 | S | * | 9/1998 | Solano ....................... D24/110 |
| 5,803,063 | A | | 9/1998 | Corey |
| 5,853,002 | A | | 12/1998 | Kawasaki |
| 5,868,131 | A | | 2/1999 | Murchie |
| 6,428,383 | B1 | * | 8/2002 | Allmon et al. .............. 446/460 |
| 6,463,928 | B1 | | 10/2002 | Buisson |
| 6,578,571 | B1 | | 6/2003 | Watt |

FOREIGN PATENT DOCUMENTS

WO    WO98/44974    10/1998
WO    WO03/080161    10/2003

\* cited by examiner

*Primary Examiner*—Justine R. Yu
*Assistant Examiner*—Shumaya B. Ali
(74) *Attorney, Agent, or Firm*—Michael I. Kroll

(57) ABSTRACT

A nebulizer device is provided for minimizing trepidation of children when using the device. The device includes a nebulizer and a housing having a shape of a toy for retaining the nebulizer therein. The housing includes an egress port connected to the nebulizer. A nebulizer delivery device is also provided and a tube is connected at a first end to the egress port and at a second end to the nebulizer delivery device for providing a liquid within the nebulizer through the egress port to the nebulizer delivery device for ingestion by a user. A carrying case having a shape corresponding to the housing is provided for storing the housing and nebulizer therein. The housing may be in the shape of one of a car, ambulance, airplane or fire engine. The carrying case may be in the shape of a garage, hospital, airplane hangar or fire house, respectively for storing the corresponding housing.

12 Claims, 15 Drawing Sheets

FIG. 3

NEBULIZER DELIVERY DEVICE

BACKGROUND OF THE INVENTION

1. Field of the Invention

The present invention relates generally to nebulizer delivery devices and, more specifically, to a toy like device to augment the delivery of medication to pediatric patients such as young children and toddlers comprising a toy like housing having a compartment for a nebulizer in communication with an egress port. Also provided is a carrying case correlated with the toy and including storage for instrumental elements.

2. Description of the Prior Art

Numerous other nebulizer delivery devices are designed for the same purpose as the present invention. Typical of these is U.S. Pat. No. 165,799 issued to Daniels on Jul. 20, 1875.

Another patent was issued to Leon on Apr. 16, 1918 as U.S. Pat. No. 1,263,079. U.S. Pat. No. 4,119,096 was issued to Drews on Oct. 10, 1978 and still yet another patent was issued on Sep. 29, 1981 to Kistler as U.S. Pat. No. 4,291,688.

Another patent was issued to Takahashi et al. on May 17, 1994 as U.S. Pat. No. 5,312,281. Yet another U.S. Pat. No. 5,803,063 was issued to Corey on Sep. 8, 1998. Another patent was issued to Kawasaki on Dec. 29, 1998 as U.S. Pat. No. 5,853,002 and still yet another was issued on Feb. 9, 1999 to Murchie U.S. Pat. No. 5,868,131.

Another patent was issued to Buisson on Oct. 15, 2002 as U.S. Pat. No. 6,463,928. Yet another U.S. Pat. No. 6,578,571 was issued to Watt on Jun. 17, 2003. Another was issued to Butler on Oct. 15, 1998 as PCT Patent No. WO 98/44974 and still yet another was issued on 2 Oct. 2003 to Bacon as PCT Patent No. WO 03/080161.

U.S. Pat. No. 165,799

Inventor: Taylor E. Daniels

Issued: Jun. 5, 1875

The inhaler, consisting of a case, the internal box, provided with the perforations and the absorbent materials and the sliding tube or mouth, constructed and operating substantially as shown.

U.S. Pat. No. 1,263,079

Inventor: Leon S. Leon

Issued: Apr. 19, 1918

An inhaler comprising a casing having formed therein a liquid receptacle and an atomizing chamber, the walls of said chamber being narrowed to a neck and terminating in a discharge opening, an independent stationary deflector formed in the wall of said atomizing chamber and projecting at an angle therefrom toward the center of said chamber and means beneath said deflector for atomizing the liquid in the receptacle and discharging the vapor therefrom through the aforesaid discharge opening.

U.S. Pat. No. 4,119,096

Inventor: Wolf Dietrich Drew

Issued: Oct. 10, 1978

An inhalator is constructed with an outer housing and an inner protective housing. The outer housing includes an opening adapted to receive the anatomy of the nasal region. The outer housing also contains a reservoir for holding a supply of medicinal liquid. The inner housing contains and protects an oscillator which energizes an electromechanical transducer, the transducer extending through a wall of the protective housing in sealed relation thereto and carrying a vibratory atomizing member which is positioned to receive liquid from the reservoir. The oscillator includes a position sensitive on-off switch which permits operation only when the inhalator is in a predetermined orientation. A droplet shield is positioned forward of the atomizing member, between the atomizing member and the opening in the outer housing so that liquid droplets of the aerosol and respiration moisture precipitate thereon and run off along a path over which the droplets will not strike the atomizing member.

U.S. Pat. No. 4,291,688

Inventor: Frederic E. Kistler

Issued: Sep. 29, 1981

An inhalation device of the type adapted to receive and locate an aerosol container designed to administer a multiplicity of metered doses, said aerosol container having a composition under pressure therein and having metering valve means including a valve stem and associated metering means, the valve stem having an axial discharge tube extending therethrough for discharge of a metered dose upon actuation of said metering valve means by depression of said valve stem, said inhalation device comprising a body having a skirt adapted to receive and locate said aerosol container in a first end thereof and a head-piece connected to a second end of said skirt, a mouth-piece extending from said head-piece and in communication therewith, and an audible signal generating means, said head-piece having actuating means for said metering valve means and a discharge passageway leading to a discharge orifice directed towards said mouth-piece, said actuating means being engageable with the valve stem upon location of the container within the skirt and operable to actuate the metering valve means whereby a metered dose is discharged through the valve stem discharge tube and the discharge passageway and discharge orifice into the mouth-piece, wherein said audible signal generating means is located in said air-passageway within the body upstream of said discharge orifice and surrounds the actuating means for the metering valve means, and is actuatable upon inhalation through said mouth-piece when said inhalation device is in engagement with said container.

U.S. Pat. No. 5,312,281

Inventor: Minoru Takahashi et al.

Issued: May 17, 1994

An ultrasonic wave nebulizer for converting water or liquid to mist has a disc-shaped piezoelectric vibrator (TD) which has a pair of surfaces one of which is defined as an operation surface. A thin plate (21) having a plurality of small holes or mesh is located close to the operation surface so that a gap or a thin water or liquid film is defined between the mesh and the operation surface. The gap spacing is smaller than the diameter of a water drop which is composed by surface tension of water where no mesh is located. Upon excitation of the vibrator with high frequency power, the water film is converted to mist. The exciting frequency is almost the same as the resonant frequency of the vibrator. The high frequency power is intermittent having duty ratio ($D_{ON}/D$) in the range from 10% to 70% so that instantaneous exciting power is high to facilitate water to mist conversion while average power is low to keep temperature at the operation surface low. The present nebulizer has many applications, including medical inhaler, a toy which generates pseudo smoke, etc.

U.S. Pat. No. 5,803,063

Inventor: Craig Corey

Issued: Sep. 8, 1998

There is provided a device to augment the delivery of medication to a patient in aerosolized or gaseous form. The device includes a means, such as a nebulizer, for supplying medication coupled to the mouthpiece of a telephone-shaped handle. The telephone-shaped handle has a gripping portion, an earpiece at one end and a mouthpiece at the other end. The earpiece may include means to generate music or the like. The delivery device is especially useful for use with small children and infants.

U.S. Pat. No. 5,853,002

Inventor: Mary Kelly Kawasaki

Issued: Dec. 29, 1998

A pediatric nebulizer enhancer (10) comprising a T-fitting (12). A structure (14) is for mounting a first end (16) of the T-fitting (12) to a dome cover (18) on a dome (20), which holds medication and saline, that is connected to an end of a tubing (21) from an oxygen outlet. A plug (22) is for sealing off a second end (24) of the T-fitting (12). A facility (26) on a third end (28) of the T-fitting (12) is for spraying a medicated mist (29) directly into a face (30) of a child (32). The child (32) can focus onto the spraying facility (26) without any fear, by being attracted to the spraying facility (26).

U.S. Pat. No. 5,868,131

Inventor: Barry Joseph Murchie

Issued: Feb. 9, 1999

An infant breathing aid assembly comprising an infant soother having a safety shield with at least one vent cooperates with a decongestant module having a housing for housing vapor emitting medicine and fixing means adapted to be retentively received in the vent for fixing the housing to the infant soother. In use the housing closely abuts the safety shield to substantially seal the vapor emitting medicine within the housing and the safety shield, and the housing emits vapor from the medicine.

U.S. Pat. No. 6,463,928

Inventor: Michael Irwin Buisson

Issued: Oct. 15, 2002

The Pediatric Prepatory and Induction Anesthesia Device ("PPIAD") is designed to aid anesthetists in effectively administering anesthetic gas to young patients. The PPIAD has a toy-like appearance, which calms the fears of children. The PPIAD also incorporates toy-like devices such as whistles and balloons. When the PPIAD is given to children prior to treatment, the child can play with it as a toy. During this play time, the PPIAD actually teaches the child proper breathing for the administration of anesthetic gas because the whistle and balloon are only activated by deep breathing. Thus, when the child is administered anesthetic gas with the PPIAD, the application of anesthetic gas is much more effective. In addition, as the anesthetic gas is applied with the PPIAD, the child is encouraged to breathe deeply to activate the toy-like devices, enhancing the application of anesthetic gas to the child. Thus, the PPIAD helps doctors provide effective care for child patients as it clams the fears of child patients during these medical procedures.

U.S. Pat. No. 6,578,571

Inventor: Paul M. Watt

Issued: Jun. 17, 2003

An incentive inhaler device includes an inhalation device, at least one incentive toy coupled to the inhalation device, and at least one separator. The inhalation device has a respiration device and a connector that is linkable to a delivery device. The delivery device can deliver drugs, aerosols, powder and gas. The incentive toy is respiration driven and has at least one of a visible characteristic and an audible characteristic. The separator decouples the toy from at least one component of the inhalation device to ensure directional flow of respirational air which drives the toy. The separator can include a valve, a filter, or a baffle.

PCT Patent Number 98/44974

Inventor: Bruce Butler

Issued: 15 Oct. 1998

An apparatus for inducing a pediatric to inhale a fluid pharmacological agent through a face mask. The apparatus comprises a fluid conduit through which fluid pharmacological agent may be inhaled, a sensory patient stimulator coupled to said conduit and actuated by inspiratory or expiratory flow through said conduit.

PCT Patent Number 03/080161

Inventor: Raymond Bacon

Issued: 2 Oct. 2003

A dispenser comprising a can and a body. The can is an aluminum extrusion with a valve crimped into its mouth, the valve having an outlet spout. The crimped region of the can surrounding the valve has a lesser diameter than the can has through the main part of its length. The body has a mouthpiece with a pivotal cover drivingly connected to a cam. This bears on the underside of a junction member into a socket of which the spout fits. A breath actuated dose release mechanism is provided. The body has a tubular section for receiving the necked down region of the can. The tubular section and the main part of the can having the same external diameter. A printed paper label coated with self adhesive is wrapped around the joint between the body and the can to unit the can to the body in position such that when the cover is open, a dose is dispensed by the cam lifting the junction member and depressing the spout. In order to establish correct positioning of the can with respect to the body, prior to positioning of the label, a predetermined force is applied to ensure that the spout is fully depressed. This causes the can to release into the release mechanism a dose, which will usually be a metered dose. Thus in this position of the can in the body, when the cover is in use, another dose will be released. With the force still applied the label is applied to the can and the body fixing their relative position.

While these devices may be suitable for the purposes for which they were designed, they would not be as suitable for the purposes of the present invention, as hereinafter described. The present invention is a toy like device to augment the delivery of medication to a pediatric patient such as young children and toddlers including a toy like housing having a compartment for a nebulizer in communication with an egress port. Also provided is a carrying case having correlated with the toy with storage for instrumental elements.

SUMMARY OF THE PRESENT INVENTION

A primary object of the present invention is to provide a toy like device to augment the delivery of medication to pediatric patients such as young children and toddlers.

Another object of the present invention is to provide a nebulizer that will minimize the fear of using such a device from young children and toddlers.

Yet another object of the present invention is to provide a device comprising a toy like housing having a compartment for a nebulizer in communication with an egress port.

Still yet another object of the present invention is to provide a carrying case having a correlation to the toy.

Another object of the present invention is to provide a carrying case correlated with the toy and including storage for instrumental elements.

Additional objects of the present invention will appear as the description proceeds.

The present invention overcomes the shortcomings of the prior art by providing a toy like device for augmenting the delivery of medication to a pediatric patient such as young children and toddlers comprising a toy like housing having a compartment for a nebulizer in communication with an egress port. Also provided is a carrying case correlated with the toy for storing instrumental elements.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

Figure 3:
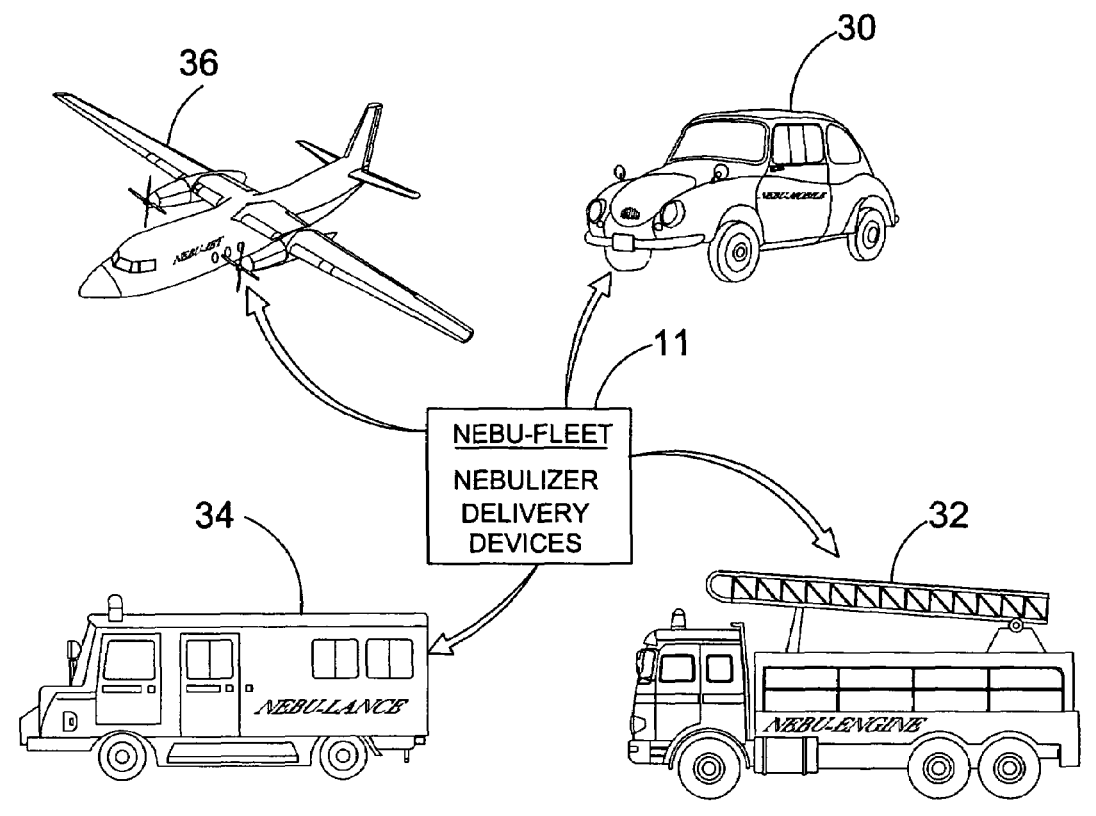

FIG. 3 is an illustrative view of nebulizers for use with the nebulizer delivery device of the present invention;

DESCRIPTION OF THE REFERENCED NUMERALS

Figure 1:
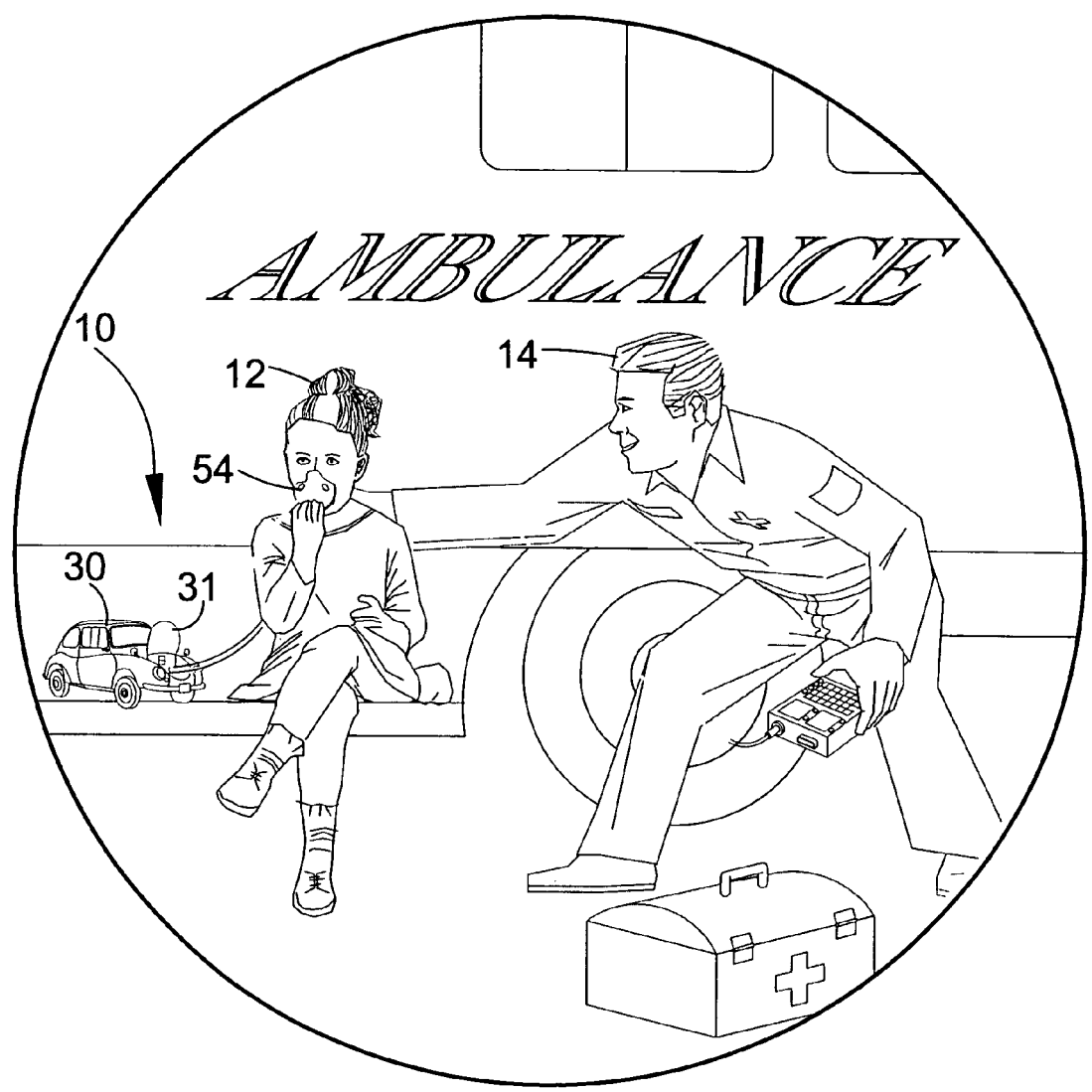
FIG. 1 is an illustrative view of the nebulizer delivery device of the present invention in use.

Turning now descriptively to the drawings, in which similar reference characters denote similar elements throughout the several views, the Figures illustrate the nebulizer delivery system of the present invention. With regard to the reference numerals used, the following numbering is used throughout the various drawing figures.

10 nebulizer delivery device of the present invention
11 nebulizer delivery device
12 child
14 caregiver
16 mouthpiece
18 T-piece
20 retractable hose
22 cap
24 baffle (jet)
26 nebulizer chamber
28 air inlet
30 car housing
31 pivotable hood
32 fire engine housing
34 ambulance housing
36 jet housing
38 garage shaped carrying case
40 storage compartments
42 adjustable strap
44 egress port
46 on/off switch
48 strap
50 trunk
52 cargo door
54 face mask
56 nose
58 back door
60 hangar shaped carrying case
62 storage compartments in hangar shaped carrying case
64 adjustable strap for hangar shaped carrying case
66 on/off switch
68 pivotable nose piece
70 cargo door
72 egress port
74 hospital shaped carrying case
76 strap
78 storage compartments in hospital shaped carrying case
80 hood door
82 on/off switch
84 back storage door
86 egress port
88 fire house shaped carrying case
90 adjustable strap for fire house shaped carrying case
92 storage compartments in fire house shaped carrying case
94 hood door
96 back door
98 on/off switch
100 egress port

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments; practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 15 illustrate a nebulizer delivery device of the present invention which is indicated generally by the reference numeral 10.

FIG. 1 is an illustrative view of a nebulizer device of the present invention in use. The present invention is a toy like device used to augment the delivery of medication to pediatric patients such as young children and toddlers. The device includes a toy like housing having a compartment for a nebulizer in communication with an egress port 31. Also provided with the device is a carrying case correlated with the toy for storage of instructional elements. The carrying case can be seen in FIGS. 4,8,11 and 14.

An illustrative view of a child using the nebulizer device 10 of the present invention is shown in FIG. 1. Shown herein, a caregiver 14 is assisting a child 12 with use of the nebulizer delivery device 10 of the present invention. The housing of the nebulizer device 10 is formed in the shape of a car 30 and includes a pivotable hood 31. A nebulizer hose 20 connects to the housing at an egress under the hood 31. A facemask 54 is connected to an end of the hose 20 opposite the connection to the housing 30. The facemask 54 is placed by the user/child 12 over the mouth to inhale a mist provided from the nebulizer device 10 through the hose 20. The mist includes but is not limited to a medicated mist, created by the nebulizer 44 shown in FIG. 6. The housing shown in FIG. 1 is in the form of a car. Alternatively, the housing may be in the shape of one of but not limited to a fire engine housing 32, an ambulance housing 34 and a jet housing 36 as will be discussed hereinafter.

FIG. 2 is an exploded view of the nebulizer delivery device 11 of the present invention. Shown is a possible configuration of parts as they may correlate with each other. Also shown is the tubing 20 which is to be utilized with a fully assembled nebulizer delivery device 11 for connecting the nebulizer delivery device 11 to the nebulizer 10.

The nebulizer delivery device 11 of the present invention includes a mouthpiece 16. The mouthpiece 16 attaches to one end of a T-piece 18. A vertical member of the T-piece 18 attaches to a cap 22 for a nebulizer chamber 26. A baffle (jet) 24 is housed inside the nebulizer chamber 26. The cap 22 connects to the nebulizer chamber 26 and the baffle 24, retaining the baffle 24 between the cap 22 and the chamber 26. Attached to the base of nebulizer chamber 26 is an external air inlet 28. One end of a retractable hose 20 connects to the air inlet 28. The other end of the retractable hose 20 connects to the egress 31 of the housing 30 as shown in FIG. 1.

As can be seen from FIG. 3, the housing may be formed in the shape of a car housing 30, a fire engine housing 32, an ambulance housing 34 and a jet housing 36. The housing, 30, 32, 34 or 36, is connected to the nebulizer delivery device 11 through a hose 20 as can be seen in FIG. 1.

FIG. 3 shows a perspective view of different shaped housings for the nebulizer device 10 of the present invention. Shown are various shapes for the housing. The housing is shaped to be a toy like device to augment the delivery of medication to pediatric patients such as young children and toddlers. The housing includes a compartment for a nebulizer in communication with an egress port 31. The nebulizer device 10 includes the housing. The housing is in the shape of one of but not limited to a car 30, a fire engine 32, an ambulance 34, and a jet 36. The shapes for the housing shown in FIG. 3 are for purposes of example only. In practice, the housing may be in any desired shape that will facilitate use by a child or toddler. When the nebulizer 44 is a jet nebulizer, the compressed air is stored in the housing. Alternatively, when the nebulizer 44 is an ultrasonic nebulizer, sound waves are generated by the housing.

FIG. 4 is an illustrative view of the nebulizer device 10 of the present invention having a housing in the shape of a car 30. The car shaped nebulizer device 10 is positioned within a carrying case 38 in the form of a garage. Shown is a nebulizer device having a car shaped housing, the car shaped housing provides a toy like device to augment the delivery of medication to pediatric patients such as young children and toddlers and having a compartment for a nebulizer in communication with an egress port. Also provided is a carrying case 38 correlated with the shape of the housing for storing for the nebulizer delivery device components and instructional elements. The carrying case 38 includes an adjustable strap 42 for storage of the nebulizer device 10 and easy transport thereof. The user can adjust the length of the strap 42 so that the nebulizer device 10 can be worn over the shoulder of the user allowing his hands to be free as needed. A plurality of storage compartments 40 are provided on the external portions of the carrying case 38. The storage compartments 40 can selectively store objects including but not limited to instructional elements and spare parts.

Figure 5:
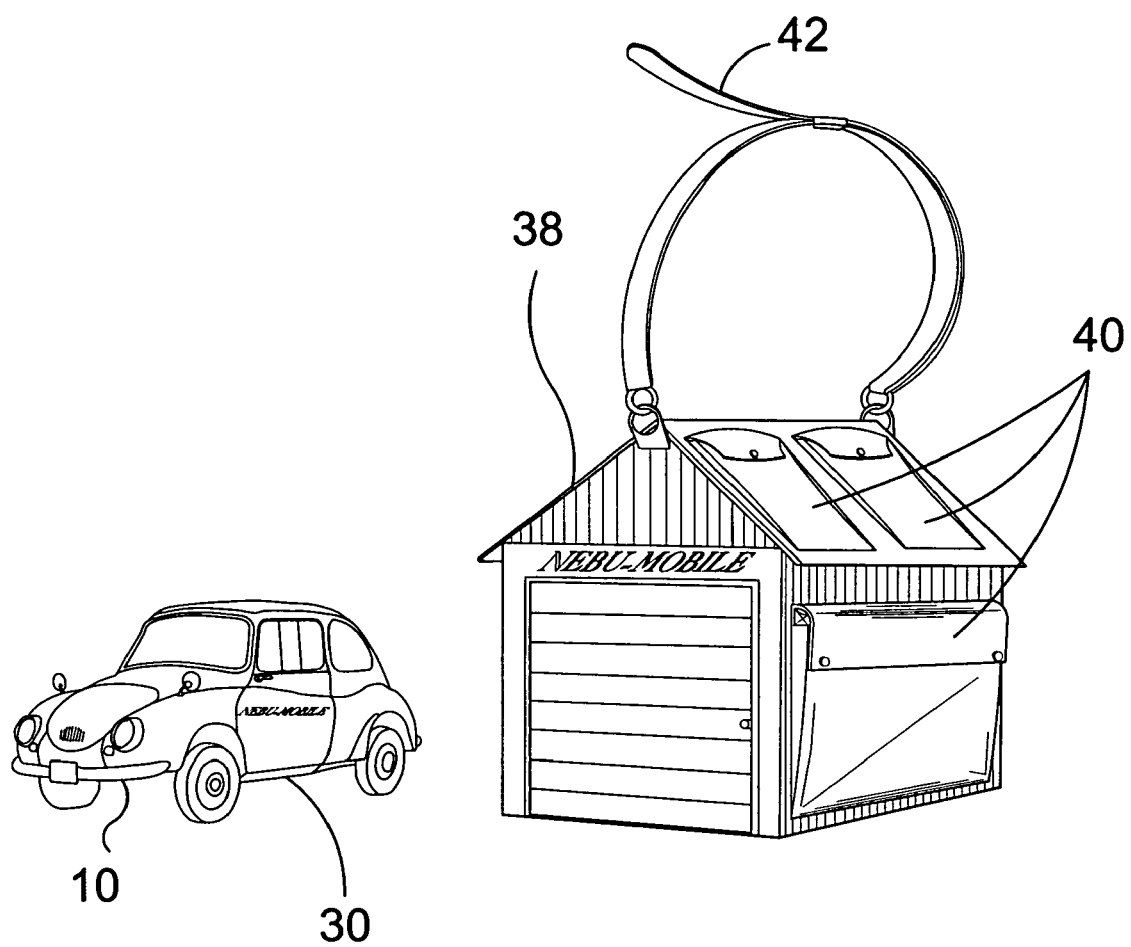
FIG. 5 is an illustrative view of a car shaped nebulizer delivery device and carrying case of the present invention.

FIG. 5 is an illustrative view of the nebulizer device 10 having a car shaped housing 30 with its carrying case 38. Shown is a nebulizer device having a car shaped housing 30, the car shaped housing 30 provides a toy like device to augment the delivery of medication to pediatric patients such as young children and toddlers comprising a toy like housing having a compartment for a nebulizer in communication with an egress port. Also provided is a carrying case correlated with the shape of the housing for storage of the nebulizer delivery device components and instructional elements. The carrying case 38 includes an adjustable strap 42 for storage of the nebulizer device 10 and easy transport thereof. The user can adjust the length of the strap 42 so that the nebulizer device 10 can be worn over the shoulder of the user allowing his hands to be free as needed. A plurality of storage compartments 40 are provided on the external portions of the carrying case 38. The storage compartments 40 can selectively store objects including but not limited to instructional elements and spare parts.

In FIG. 5 the nebulizer device 10 is shown located next to the carrying case 38. As shown herein, the nebulizer delivery device 10 has a car shaped housing 30. Prior to use, the nebulizer device 10 is removed from the carrying case 38, as shown herein. The carrying case 38 for the car housing 30 is shaped like a garage. The carrying case 38 contains an adjustable strap 42 for easy transport of the nebulizer delivery device 10. The user can adjust the strap 42 so that the carrying case 38 can be worn over the shoulder of the user allowing the user's hands to be free as needed when carrying the nebulizer device. The plurality of storage compartments 40 are provided on the external portions of the carrying case 38. The storage compartments 40 are provided for selectively retaining objects therein.

Figure 4:
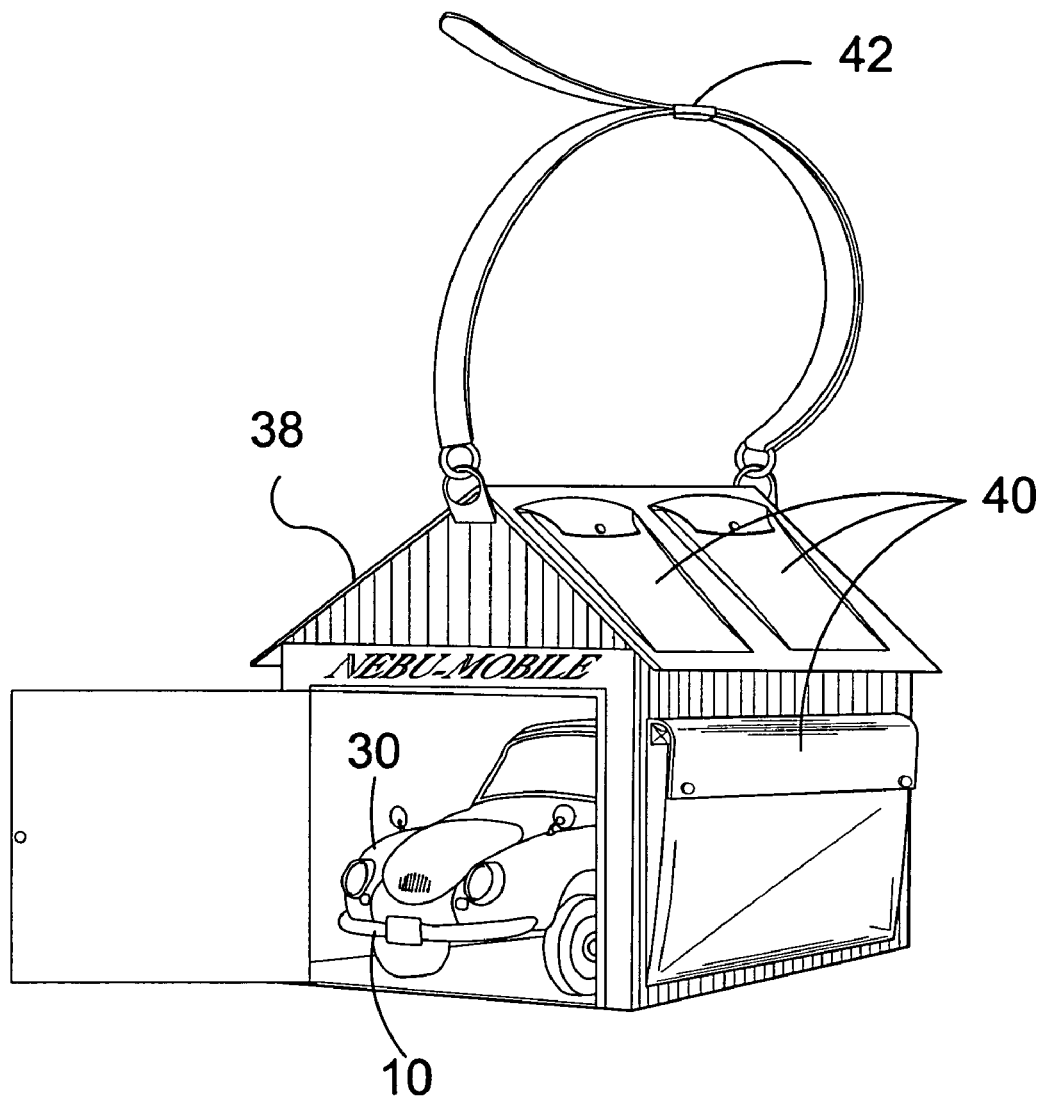
FIG. 4 is an illustrative view of a car shaped nebulizer delivery device of the present invention within its carrying case.
Figure 6:
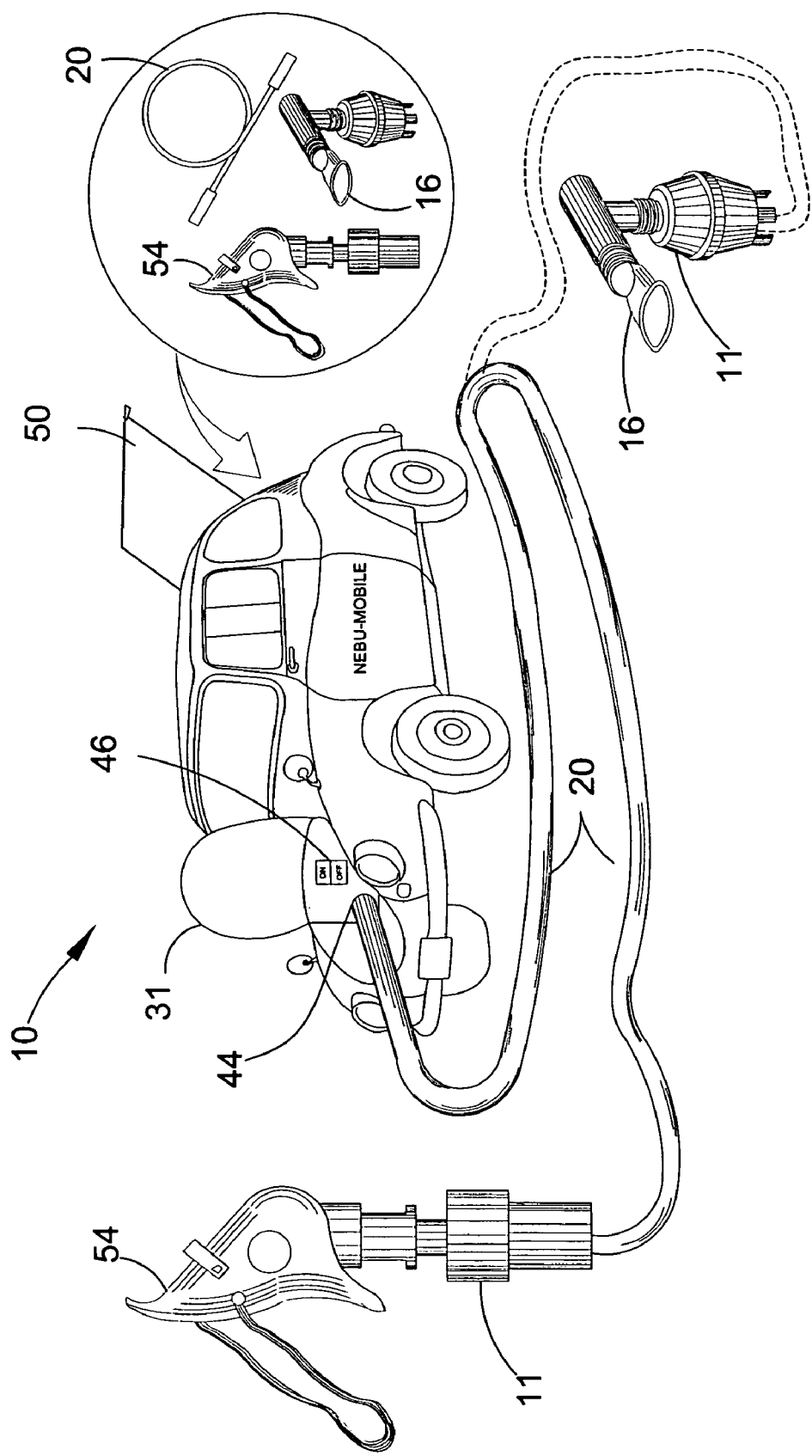
FIG. 6 is an illustrative view of a car shaped nebulizer delivery device of the present invention and including different delivery devices used with the nebulizer.

FIG. 6 is an illustrative view of the nebulizer device 10 of the present invention. Shown is the nebulizer device of the present invention having a car shaped housing 30 forming a toy like device to augment the delivery of medication to pediatric patients such as young children and toddlers. The car shaped housing 30 has a compartment for storing a nebulizer canister which is in communication with an egress port 44. Also provided is a carrying case correlated with the car shaped housing 30 for storage of the nebulizer device 10 as well as instructional elements and the delivery device. 11. The carrying case is clearly illustrated in FIGS. 4 and 5.

The nebulizer device 10 of the present invention is shown illustratively in FIG. 6 ready for use connected to a delivery device 11 via the hose 20. As shown herein, the nebulizer device 10 has a car shaped housing 30. The car shaped housing 30 includes a hood 31 and a trunk 50. The hood 31 and the trunk 50 are pivotally connected to the car shaped housing 30. Positioned beneath the hood 31 is the egress port 44 for connection of the hose 20. The nebulizer delivery device components include the facemask 54, the T-shaped nebulizer 11 with mouthpiece 16 and the retractable hose 20. These components may be stored in the trunk 50 when not in use. The mouthpiece 16 is generally used for an older child as they are better able to retain the mouthpiece 16 in their mouth. In use, a child will simply retain the mouthpiece within their mouth and breathe through the mouthpiece. Alternatively, the facemask 54 is generally used by a younger child as they are not required to put forth any effort to receive the effects of the nebulizer device 10 other than to wear the facemask 54. The facemask 54 includes a strap 48 connected on either side thereof. The strap is positioned around the head of the child when in use to retain the facemask 54 in place covering the mouth of the child. The child then only needs to breathe normally to receive the effects of the nebulizer device 10.

Figure 2:
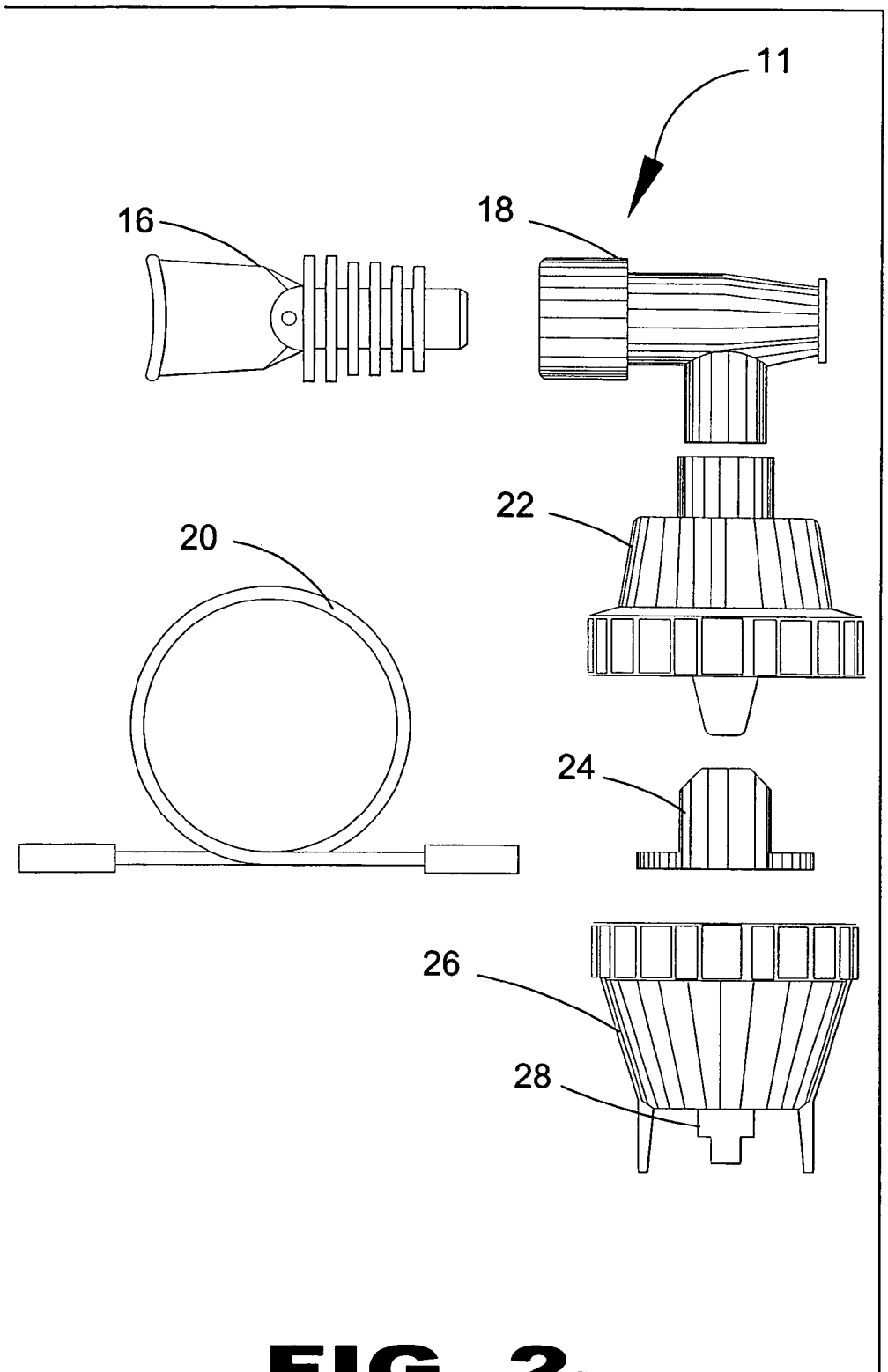
FIG. 2 is an exploded view of a nebulizer delivery device in accordance with the present invention.

The first end of the hose 20 is connected to the egress port 44 and the second end of retractable hose 20 connects to the nebulizer delivery device 11. The mouthpiece 16 or the facemask 48 is then positioned in order to cover the child's mouth. When the hood 48 is in the open position, an on/off switch 46 is exposed. When the nebulizer delivery device 11 is a jet nebulizer, the compressed air is stored in the housing. When the on/off switch 46 shown in FIG. 6 is in the "on" position, compressed air flows through the retractable hose 20 into nebulizer chamber 26 as shown in FIG. 2. The compressed air converts the liquid medication solution into a mist that can be inhaled by the child through a mouthpiece 16 or the face mask 54.

Alternatively, when the nebulizer 44 is an ultrasonic nebulizer, sound waves are generated by the housing. When the on/off switch 46 is in the "on" position, sound waves travel through the retractable hose 20 into nebulizer chamber 26 as shown in FIG. 2. The sound waves convert the liquid medication solution into a mist that can be inhaled by the child through the mouthpiece 16 or the face mask 54.

Figure 7:
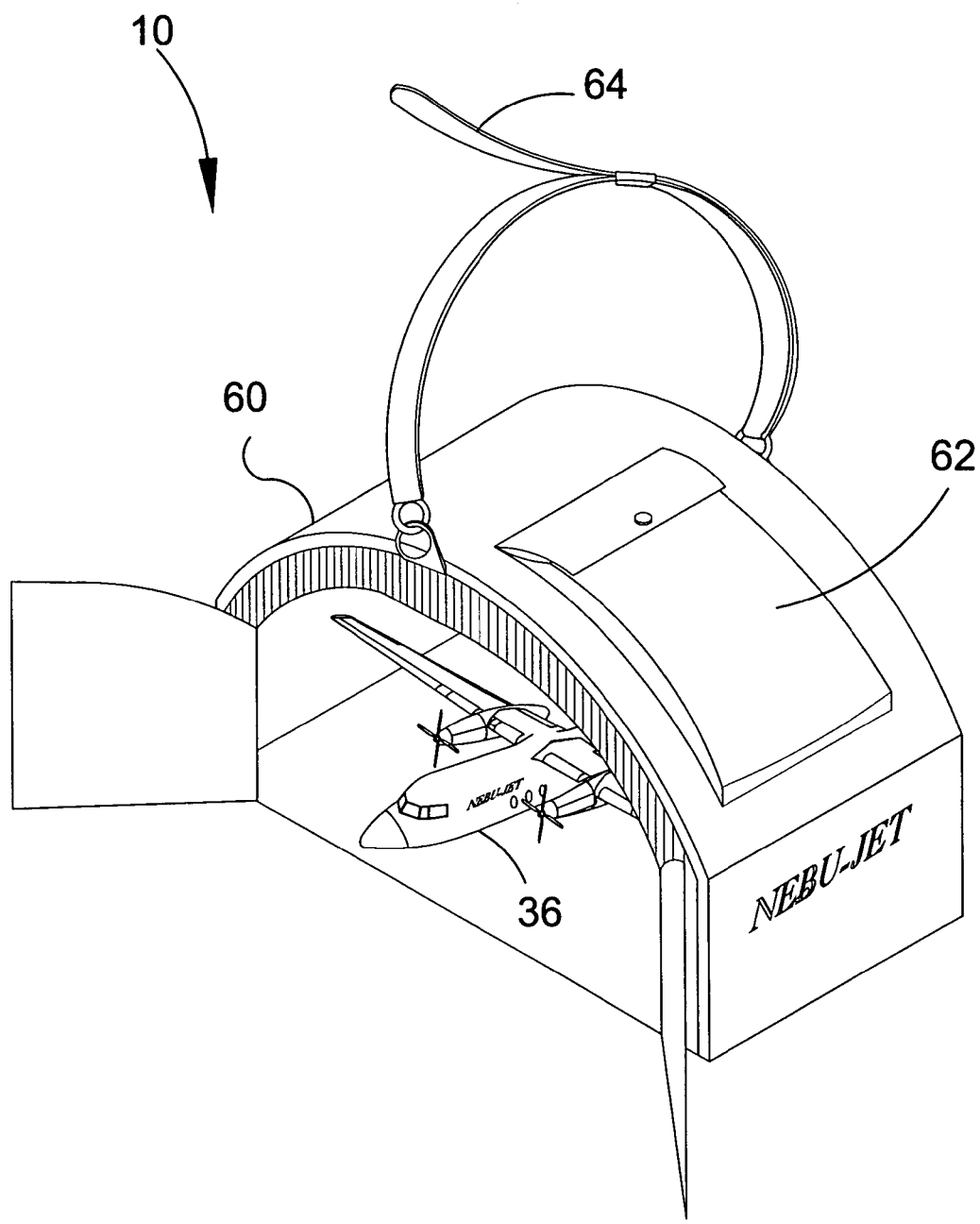
FIG. 7 is an illustrative view of a jet shaped nebulizer delivery device of the present invention within the carrying case.

FIG. 7 is an illustrative view of the nebulizer device 10 of the present invention having a housing in the shape of an airplane 36. The airplane shaped nebulizer device 10 is positioned within a carrying case 60 in the form of an airplane hangar. Shown is a nebulizer device having an airplane shaped housing 36, the airplane shaped housing provides a toy like device to augment the delivery of medication to pediatric patients such as young children and toddlers comprising a toy like housing having a compartment for a nebulizer in communication with an egress port. Also provided is a carrying case 60 correlated with the shape of the housing 36 for storage of the nebulizer delivery device as well as for instructional elements. The carrying case 60 includes an adjustable strap 64 for storage of the nebulizer device 10 and easy transport thereof. The user can adjust the length of the strap 42 so that the nebulizer device 10 can be worn over the shoulder of the user allowing for hands free carrying of the nebulizer device as needed. A plurality of storage compartments 62 are provided on the external portions of the carrying case 60. The storage compartments 62 can selectively store objects including but not limited to instructional elements and spare parts.

Figure 8:
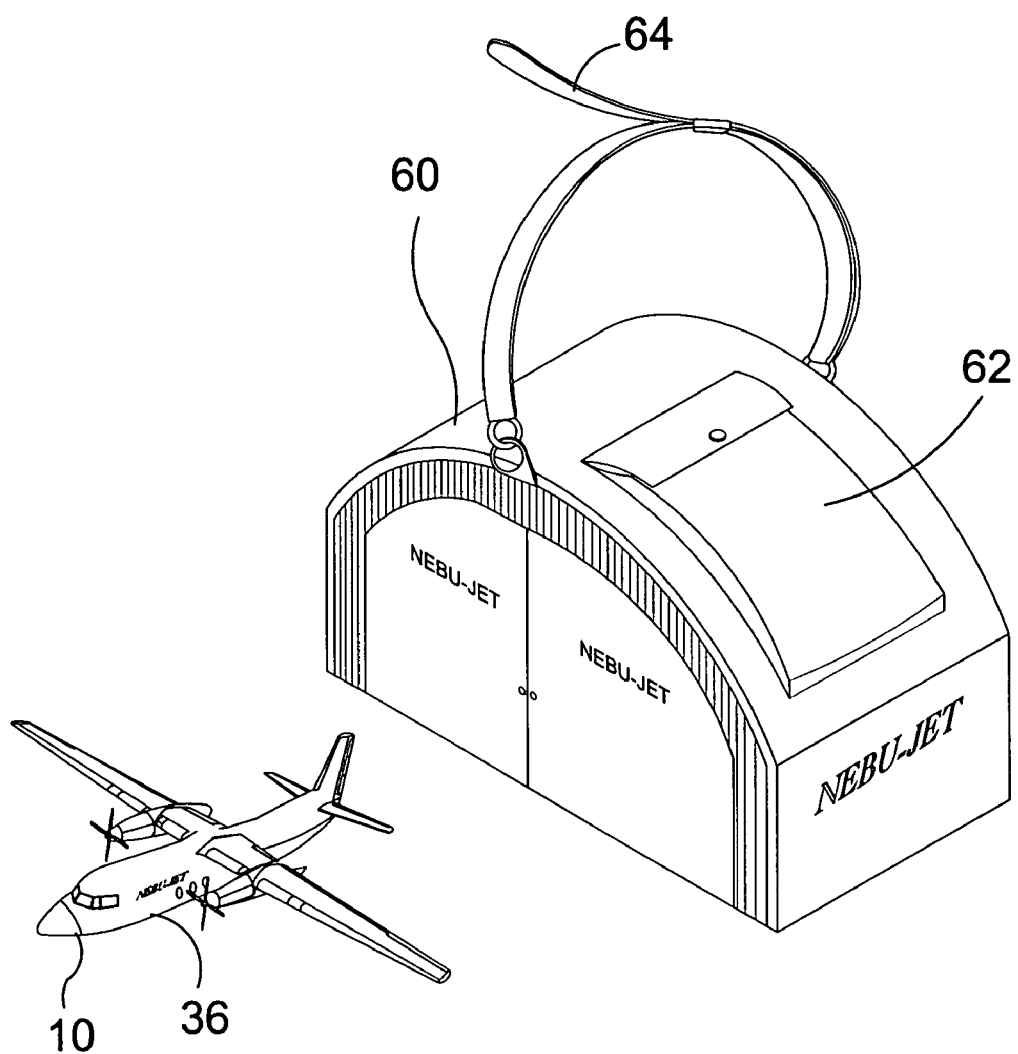
FIG. 8 is an illustrative view of a jet shaped nebulizer delivery device and carrying case of the present invention.

FIG. 8 is an illustrative view of the nebulizer device 10 having an airplane shaped housing 36 with its carrying case 60. Shown is a nebulizer device having an airplane shaped housing 36, the airplane shaped housing provides a toy like device to augment the delivery of medication to pediatric patients such as young children and toddlers comprising a toy like housing having a compartment for a nebulizer in communication with an egress port. Also provided is a carrying case 60 correlated with the shape of the housing for storage of the nebulizer delivery device components and instructional elements. The carrying case 60 includes an adjustable strap 64 for storage of the nebulizer device 10 and easy transport thereof. The user can adjust the length of the strap 64 so that the nebulizer device 10 can be worn over the shoulder of the user allowing his hands to be free as needed. A plurality of storage compartments 62 are provided on the external portions of the carrying case 60. The storage compartments 64 can selectively store objects including but not limited to instructional elements and spare parts.

In FIG. 8 the nebulizer device 10 is shown located next to the carrying case 60. As shown herein, the nebulizer delivery device 10 has an airplane shaped housing 36. Prior to use, the nebulizer device 10 is removed from the carrying case 60, as shown herein. The carrying case 60 for the airplane shaped housing 36 is shaped like an airplane hangar. The carrying case 60 contains an adjustable strap 64 for easy transport of the nebulizer delivery device 10. The user can adjust the strap 64 so that the carrying case 60 can be worn over the shoulder of the user allowing the user's hands to be free as needed when carrying the nebulizer device. The plurality of storage compartments 62 are provided on the external portions of the carrying case 60. The storage compartments 62 are provided for selectively retaining objects including but not limited to instructional elements and spare parts.

Figure 9:
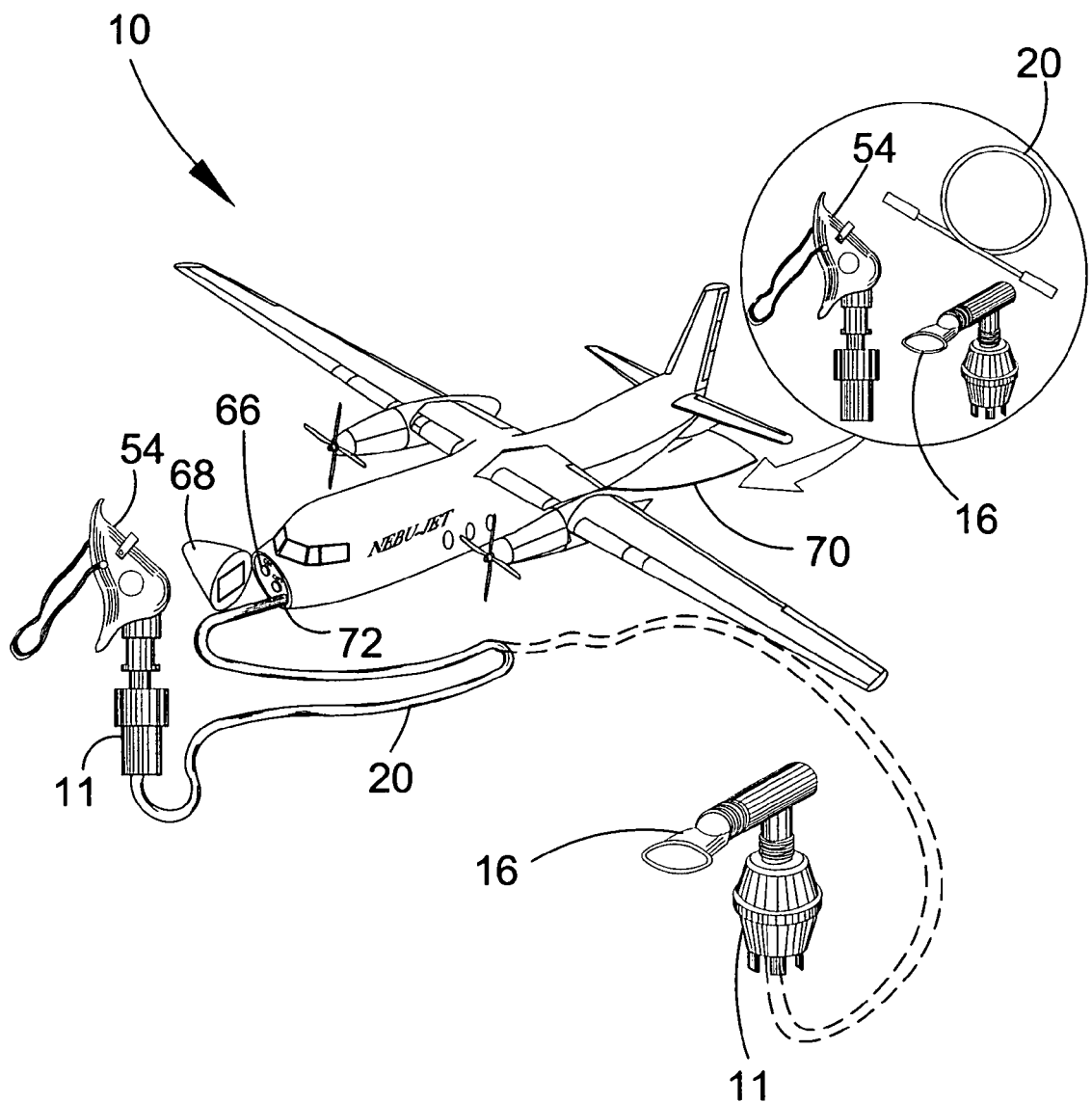
FIG. 9 is an illustrative view of a jet shaped nebulizer delivery device of the present invention along with different nebulizers able to be connected to the nebulizer delivery device.

FIG. 9 is an illustrative view of the nebulizer device 10 of the present invention. Shown is the nebulizer device of the present invention having an airplane shaped housing 36 forming a toy like device to augment the delivery of medication to pediatric patients such as young children and toddlers. The airplane shaped housing 36 has a compartment for storing a nebulizer canister which is in communication with an egress port 72. Also provided is a carrying case 60 correlated with the airplane shaped housing 36 for storage of the nebulizer device 10 as well as instructional elements and the delivery device. The carrying case is clearly illustrated in FIGS. 7 and 8.

The nebulizer device 10 of the present invention is shown illustratively in FIG. 9 ready for use connected to a delivery device 11 via the hose 20. As shown herein, the nebulizer device 10 has an airplane shaped housing 36. The airplane shaped housing 36 includes a nose compartment and a cargo area. The nose compartment is selectively accessed through the nose compartment door 68 which is pivotally connected to the housing 36. The cargo area is selectively accessed through the cargo door 70 which is pivotally connected to the housing 36. Positioned within the nose compartment is the egress port 72 for connection of the hose 20. The nebulizer delivery device components include the facemask 54, the T-shaped nebulizer 11 with mouthpiece 16 and the retractable hose 20. These components may be stored in the cargo area 70 when not in use. The mouthpiece 16 is generally used for an older child as they are better able to retain the mouthpiece 16 in their mouth. In use, a child will simply retain the mouthpiece within their mouth and breathe through the mouthpiece. Alternatively, the facemask 54 is generally used by a younger child as they are not required to put forth any effort to receive the effects of the nebulizer device 10 other than to wear the facemask 54. The facemask 54 includes a strap 48 connected on either side thereof. The strap 48 is positioned around the head of the child when in use to retain the facemask 54 in place covering the mouth of the child. The child then only needs to breathe normally to receive the effects of the nebulizer device 10.

The first end of the hose 20 is connected to the egress port 72 and the second end of retractable hose 20 connects to the nebulizer delivery device 11. The mouthpiece 16 or the facemask 48 is then positioned in or to cover the child's mouth. When the nose compartment door is in the open position, an on/off switch 66 is exposed. When the nebulizer delivery device 11 is a jet nebulizer, the compressed air is stored in the housing. When the on/off switch 66 shown in FIG. 6 is in the "on" position, compressed air flows through the retractable hose 20 into nebulizer chamber 26 as shown in FIG. 2. The compressed air converts the liquid medication solution into a mist that can be inhaled by the child through a mouthpiece 16 or the face mask 54.

Alternatively, when the nebulizer 44 is an ultrasonic nebulizer, sound waves are generated by the housing. When the on/off switch 66 is in the "on" position, sound waves travel through the retractable hose 20 into nebulizer chamber 26 as shown in FIG. 2. The sound waves convert the liquid medication solution into a mist that can be inhaled by the child through the mouthpiece 16 or the face mask 54.

Figure 10:
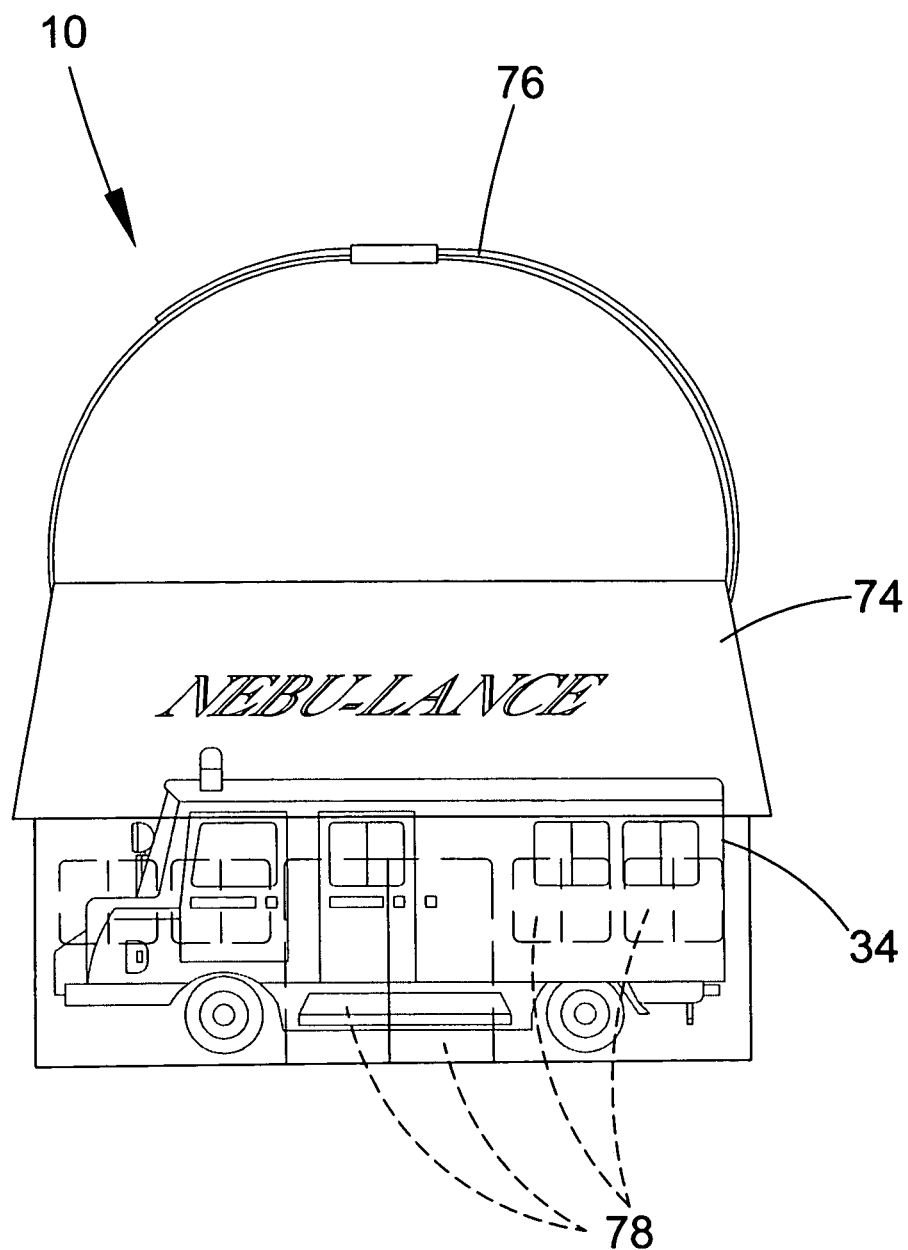
FIG. 10 is an illustrative view of an ambulance shaped nebulizer delivery device within the carrying case of the present invention.

FIG. 10 is an illustrative view of the nebulizer device 10 of the present invention having a housing in the shape of an ambulance 34. The ambulance shaped nebulizer device 10 is positioned within a carrying case 74 in the form of an ambulance garage. Shown is a nebulizer device having an ambulance shaped housing 34, the ambulance shaped housing provides a toy like device to augment the delivery of medication to pediatric patients such as young children and toddlers comprising a toy like housing having a compartment for a nebulizer in communication with an egress port. Also provided is a carrying case 74 correlated with the shape of the housing 34 for storage of the nebulizer delivery device as well as for instructional elements. The carrying case 74 includes an adjustable strap 76 for storage of the nebulizer device 10 and easy transport thereof. The user can adjust the length of the strap 76 so that the nebulizer device 10 can be worn over the shoulder of the user allowing for hands free carrying of the nebulizer device as needed. A plurality of storage compartments 78 are provided on the external portions of the carrying case 74. The storage compartments 78 can selectively store objects including but not limited to instructional elements and spare parts.

Figure 11:
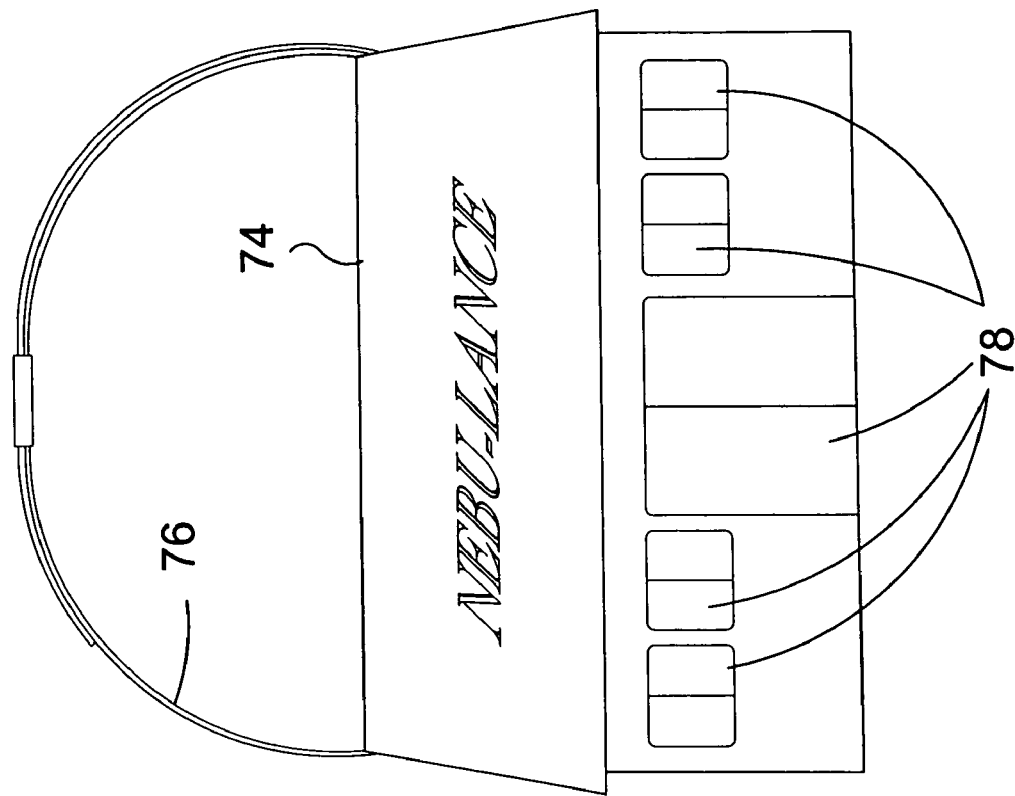
FIG. 11 is an illustrative view of an ambulance shaped nebulizer delivery device and carrying case of the present invention.
Figure 11:
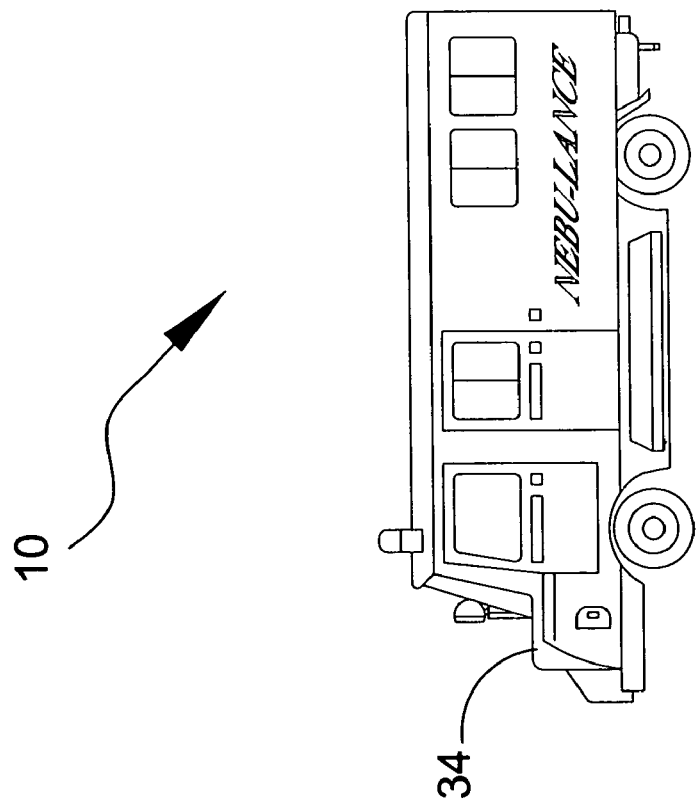

FIG. 11 is an illustrative view of the nebulizer device 10 having an ambulance shaped housing 34 with its carrying case 74. Shown is a nebulizer device having an ambulance shaped housing 34, the ambulance shaped housing provides a toy like device to augment the delivery of medication to pediatric patients such as young children and toddlers comprising a toy like housing having a compartment for a nebulizer in communication with an egress port. Also provided is a carrying case 74 correlated with the shape of the housing for storage of the nebulizer delivery device components and instructional elements. The carrying case 74 includes an adjustable strap 76 for storage of the nebulizer device 10 and easy transport thereof. The user can adjust the length of the strap 76 so that the nebulizer device 10 can be worn over the shoulder of the user allowing his hands to be free as needed. A plurality of storage compartments 78 are provided on the external portions of the carrying case 74. The storage compartments 76 can selectively store objects including but not limited to instructional elements and spare parts.

In FIG. 11 the nebulizer device 10 is shown located next to the carrying case 74. As shown herein, the nebulizer delivery device 10 has an ambulance shaped housing 34. Prior to use, the nebulizer device 10 is removed from the carrying case 74, as shown herein. The carrying case 74 for the ambulance shaped housing 34 is shaped like an ambulance garage. The carrying case 74 contains an adjustable strap 76 for easy transport of the nebulizer delivery device 10. The user can adjust the strap 76 so that the carrying case 74 can be worn over the shoulder of the user allowing the user's hands to be free as needed when carrying the nebulizer device. The plurality of storage compartments 78 are provided on the external portions of the carrying case 74. The storage compartments 78 are provided for selectively retaining objects including but not limited to instructional elements and spare parts.

Figure 12:
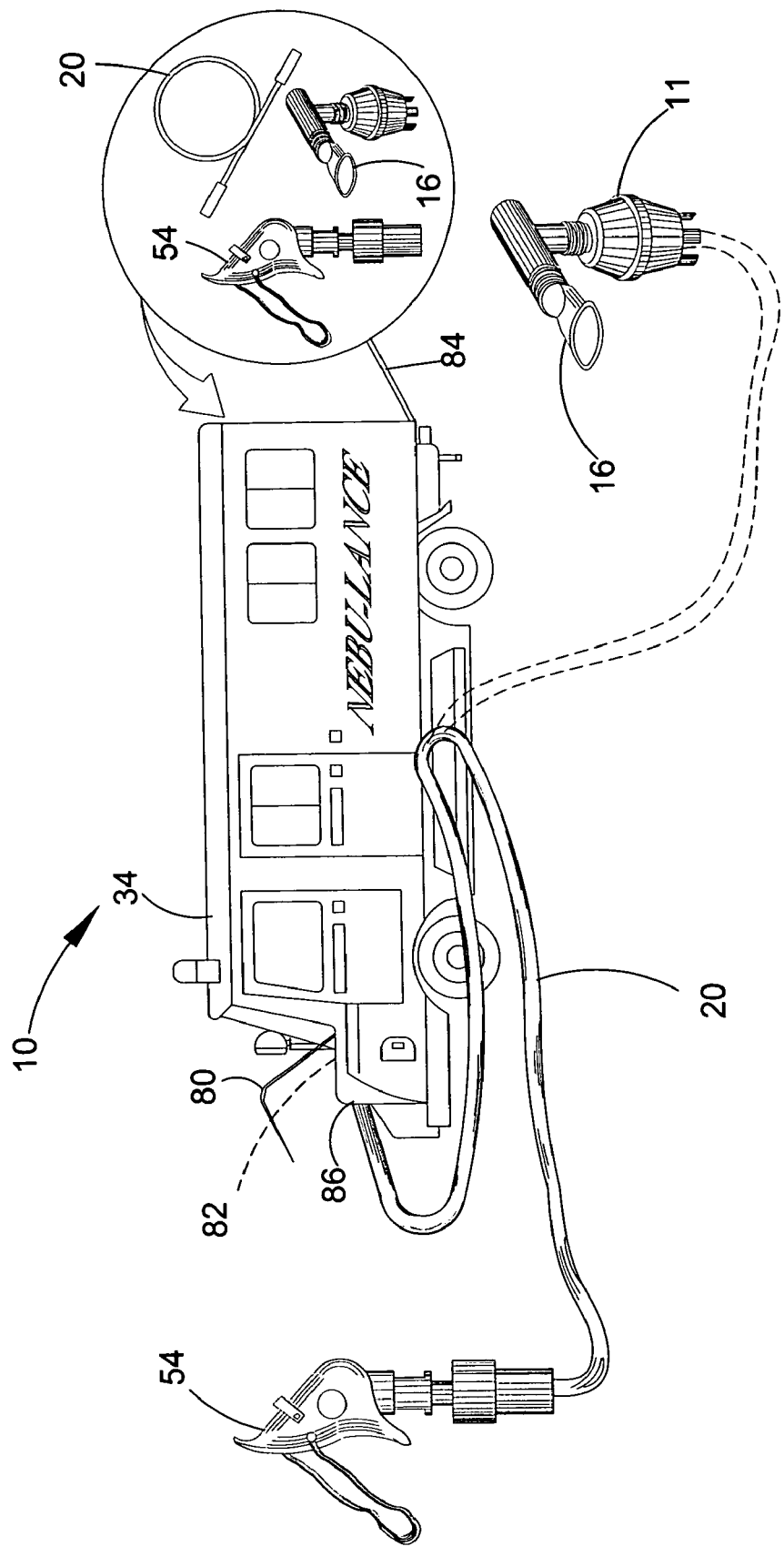
FIG. 12 is an illustrative view of an ambulance shaped nebulizer delivery device of the present invention along with different nebulizers able to be connected to the nebulizer delivery device.
Figure 13:
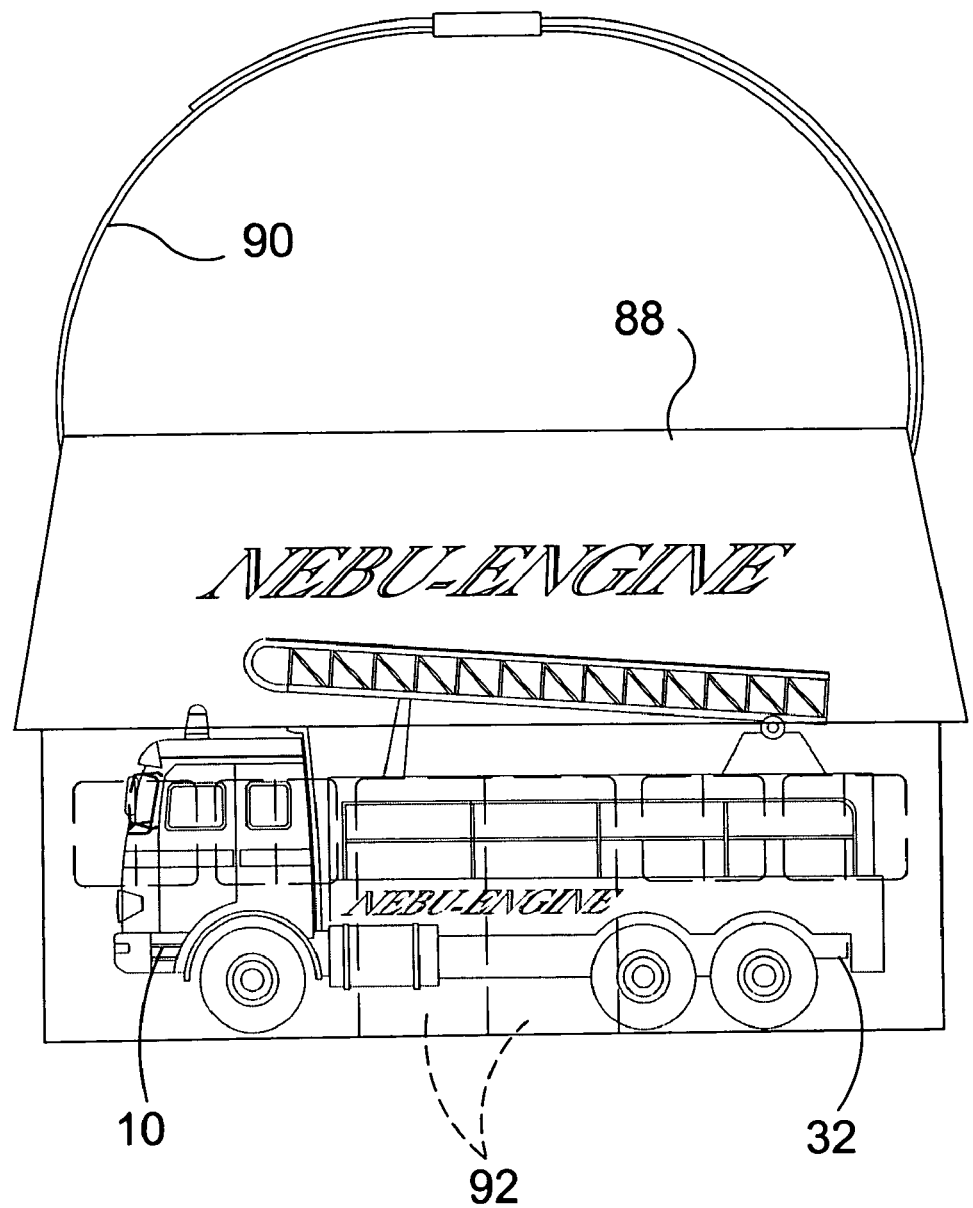
FIG. 13 is an illustrative view of a fire truck shaped nebulizer delivery device within the carrying case of the present invention.
Figure 14:
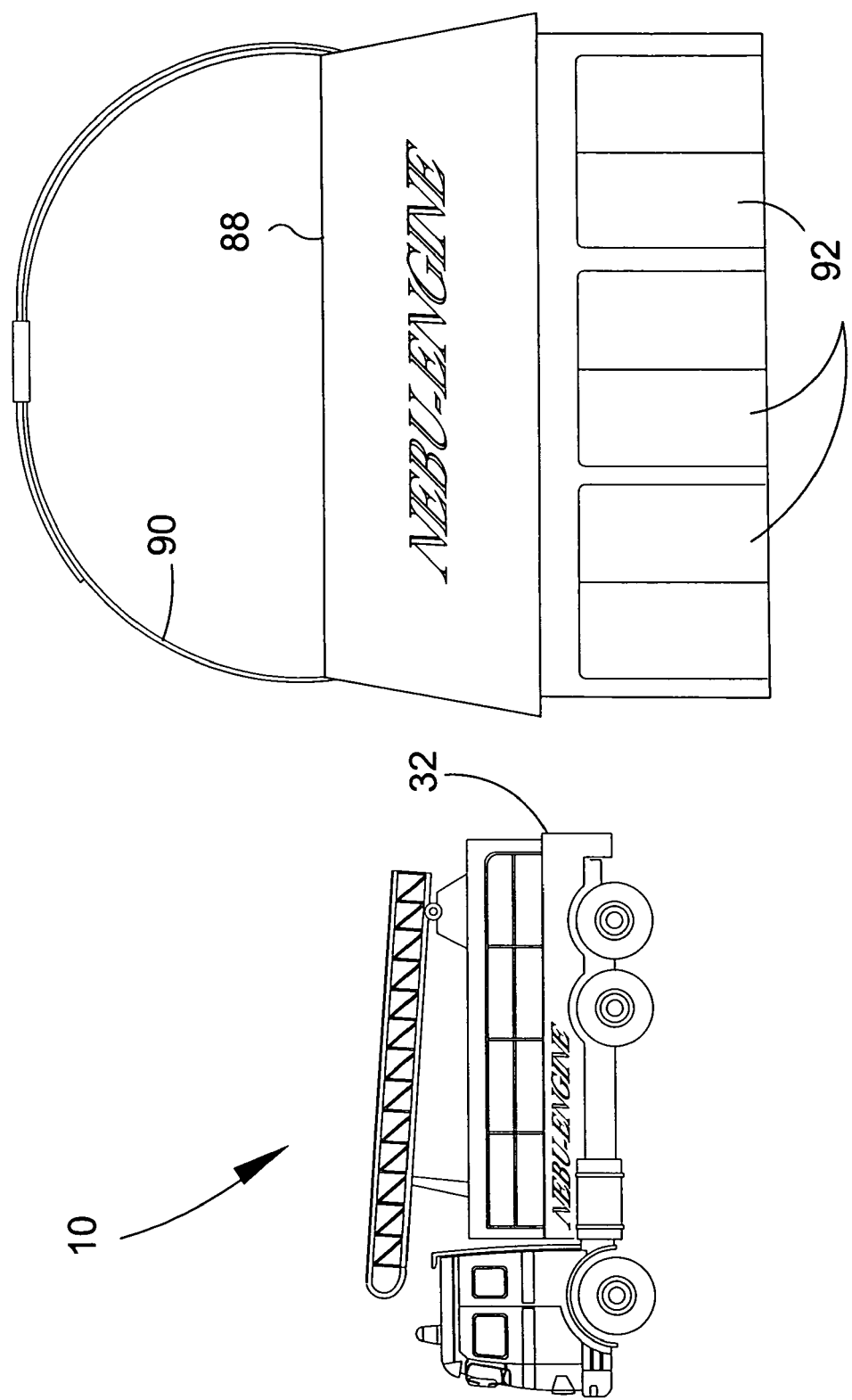
FIG. 14 is an illustrative view of a fire truck shaped nebulizer delivery device and carrying case of the present invention.

FIG. 12 is an illustrative view of the nebulizer device 10 of the present invention. Shown is the nebulizer device of the present invention having an ambulance shaped housing 34 forming a toy like device to augment the delivery of medication to pediatric patients such as young children and toddlers. The ambulance shaped housing 34 has a compartment for storing a nebulizer canister which is in communication with an egress port 72. Also provided is a carrying case 74 correlated with the ambulance shaped housing 34 for storage of the nebulizer device 10 as well as instructional elements and the delivery device. The carrying case is clearly illustrated in FIGS. 10 and 11.

The nebulizer device 10 of the present invention is shown illustratively in FIG. 12 ready for use connected to a delivery device 11 via the hose 20. As shown herein, the nebulizer device 10 has an ambulance shaped housing 34. The ambulance shaped housing 34 includes a hood compartment and a back storage area. The hood compartment is selectively accessed through the hood 80 which is pivotally connected to the housing 34. The back storage area is selectively accessed through the back door 84 which is pivotally connected to the housing 34. Positioned within the hood compartment is the egress port 86 for connection of the hose 20. The nebulizer delivery device components include the facemask 54, the T-shaped nebulizer 11 with mouthpiece 16 and the retractable hose 20. These components may be stored in the back storage area 84 when not in use. The mouthpiece 16 is generally used for an older child as they are better able to retain the mouthpiece 16 in their mouth. In use, a child will simply retain the mouthpiece within their mouth and breathe through the mouthpiece. Alternatively, the facemask 54 is generally used by a younger child as they are not required to put forth any effort to receive the effects of the nebulizer device 10 other than to wear the facemask 54. The facemask 54 includes a strap 48 connected on either side thereof. The strap 48 is positioned around the head of the child when in use to retain the facemask 54 in place covering the mouth of the child. The child then only needs to breathe normally to receive the effects of the nebulizer device 10.

The first end of the hose 20 is connected to the egress port 86 and the second end of retractable hose 20 connects to the nebulizer delivery device 11. The mouthpiece 16 or the facemask 48 is then positioned in or to cover the child's mouth. When the nose compartment door is in the open position, an on/off switch 82 is exposed. When the nebulizer delivery device 11 is a jet nebulizer, the compressed air is stored in the housing. When the on/off switch 82 shown in FIG. 6 is in the "on" position, compressed air flows through the retractable hose 20 into nebulizer chamber 26 as shown in FIG. 2. The compressed air converts the liquid medication solution into a mist that can be inhaled by the child through a mouthpiece 16 or the face mask 54.

Alternatively, when the nebulizer 44 is an ultrasonic nebulizer, sound waves are generated by the housing. When the on/off switch 82 is in the "on" position, sound waves travel through the retractable hose 20 into nebulizer chamber 26 as shown in FIG. 2. The sound waves convert the liquid medication solution into a mist that can be inhaled by the child through the mouthpiece 16 or the face mask 54.

FIG. 13 is an illustrative view of the nebulizer device 10 of the present invention having a housing in the shape of a fire engine 32. The fire engine shaped nebulizer device 10 is positioned within a carrying case 88 in the form of a fire house. Shown is a nebulizer device having a fire engine shaped housing 32, the fire engine shaped housing provides a toy like device to augment the delivery of medication to pediatric patients such as young children and toddlers comprising a toy like housing having a compartment for a nebulizer in communication with an egress port. Also provided is a carrying case 88 correlated with the shape of the housing 32 for storage of the nebulizer delivery device as well as for instructional elements. The carrying case 88 includes an adjustable strap 90 for storage of the nebulizer device 10 and easy transport thereof. The user can adjust the length of the strap 90 so that the nebulizer device 10 can be worn over the shoulder of the user allowing for hands free carrying of the nebulizer device as needed. A plurality of storage compartments 92 are provided on the external portions of the carrying case 90. The storage compartments 92 can selectively store objects including but not limited to instructional elements and spare parts.

FIG. 14 is an illustrative view of the nebulizer device 10 having a fire engine shaped housing 32 with its carrying case 88. Shown is a nebulizer device having a fire engine shaped housing 32, the fire engine shaped housing provides a toy like device to augment the delivery of medication to pediatric patients such as young children and toddlers comprising a toy like housing having a compartment for a nebulizer in communication with an egress port. Also provided is a carrying case 88 correlated with the shape of the housing for storage of the nebulizer delivery device components and instructional elements. The carrying case 88 includes an adjustable strap 90 for storage of the nebulizer device 10 and easy transport thereof. The user can adjust the length of the strap 90 so that the nebulizer device 10 can be worn over the shoulder of the user allowing his hands to be free as needed. A plurality of storage compartments 92 are provided on the external portions of the carrying case 88. The storage compartments 88 can selectively store objects including but not limited to instructional elements and spare parts.

In FIG. 14 the nebulizer device 10 is shown located next to the carrying case 88. As shown herein, the nebulizer delivery device 10 has a housing in the shape of a fire engine 32. Prior to use, the nebulizer device 10 is removed from the carrying case 88, as shown herein. The carrying case 88 for the fire engine shaped housing 32 is shaped like a fire house. The carrying case 88 contains an adjustable strap 90 for easy transport of the nebulizer delivery device 10. The user can adjust the strap 90 so that the carrying case 88 can be worn over the shoulder of the user allowing the user's hands to be free as needed when carrying the nebulizer device. The plurality of storage compartments 92 are provided on the external portions of the carrying case 88. The storage compartments 92 are provided for selectively retaining objects including but not limited to instructional elements and spare parts.

FIG. 15 is an illustrative view of the nebulizer device 10 of the present invention. Shown is the nebulizer device of the present invention having housing in the shape of a fire engine 32 forming a toy like device to augment the delivery of medication to pediatric patients such as young children and toddlers. The fire engine shaped housing 32 has a compartment for storing a nebulizer canister which is in communication with an egress port 100. Also provided is a carrying case 88 correlated with the fire engine shaped housing 32 for storage of the nebulizer device 10 as well as instructional elements and the delivery device. The carrying case is clearly illustrated in FIGS. 13 and 14.

Figure 15:
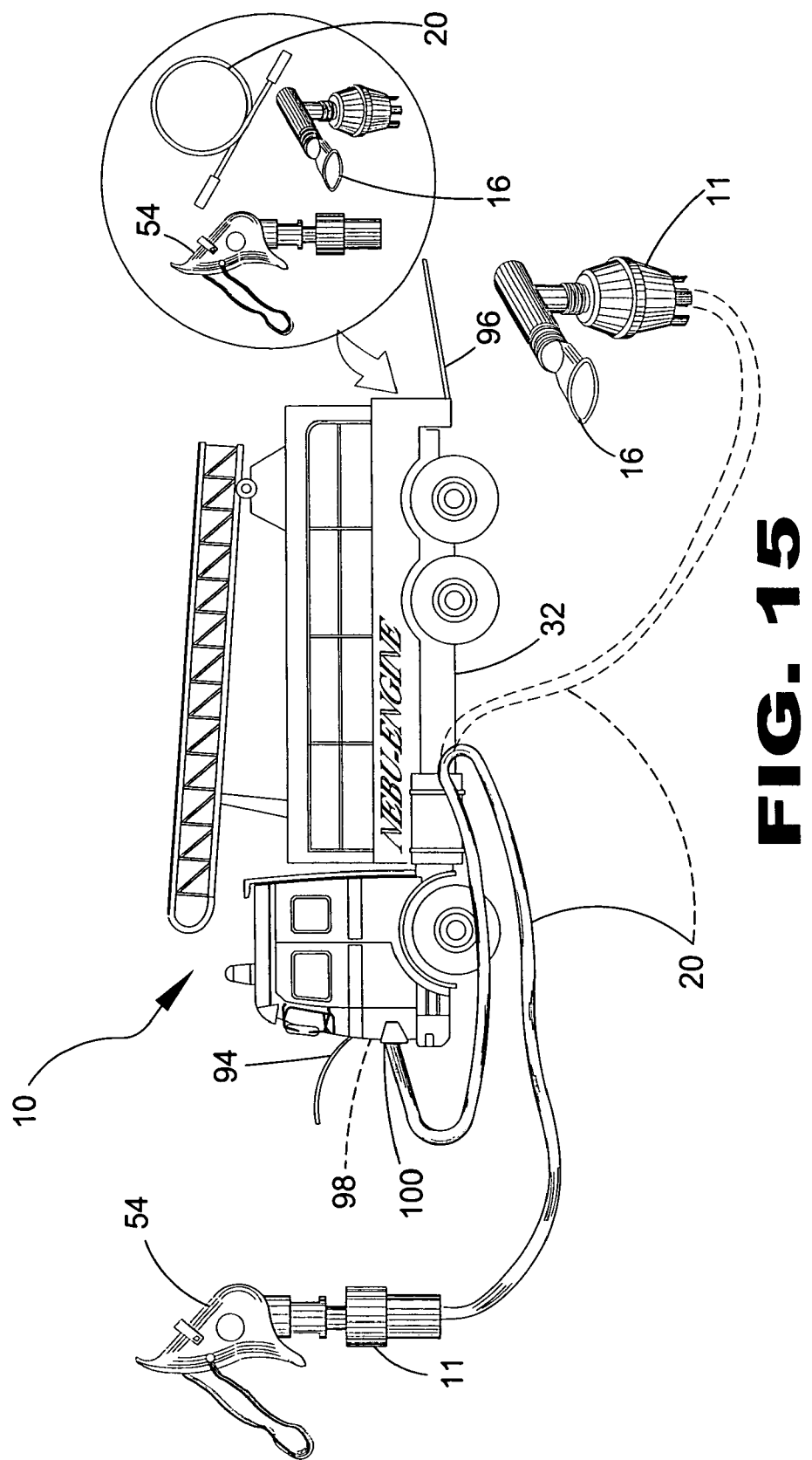
FIG. 15 is an illustrative view of a fire truck shaped nebulizer delivery the present invention along with different nebulizers able to be connected to the nebulizer delivery device.

The nebulizer device 10 of the present invention is shown illustratively in FIG. 15 ready for use connected to a delivery device 11 via the hose 20. As shown herein, the nebulizer device 10 has fire engine shaped housing 32. The fire engine shaped housing 32 includes a hood compartment and a back storage area. The hood compartment is selectively accessed through the hood door 94 which is pivotally connected to the housing 32. The back storage area is selectively accessed through the back door 96 which is pivotally connected to the housing 32. Positioned within the hood compartment is the egress port 100 for connection of the hose 20. The nebulizer delivery device components include the facemask 54, the T-shaped nebulizer 11 with mouthpiece 16 and the retractable hose 20. These components may be stored in the back storage area when not in use. The mouthpiece 16 is generally used for an older child as they are better able to retain the mouthpiece 16 in their mouth. In use, a child will simply retain the mouthpiece within their mouth and breathe through the mouthpiece. Alternatively, the facemask 54 is generally used by a younger child as they are not required to put forth any effort to receive the effects of the nebulizer device 10 other than to wear the facemask 54. The facemask 54 includes a strap 48 connected on either side thereof. The strap 48 is positioned around the head of the child when in use to retain the facemask 54 in place covering the mouth of the child. The child then only needs to breathe normally to receive the effects of the nebulizer device 10.

The first end of the hose 20 is connected to the egress port 100 and the second end of retractable hose 20 connects to the nebulizer delivery device 11. The mouthpiece 16 or the facemask 48 is then positioned in or to cover the child's mouth. When the nose compartment door is in the open position, an on/off switch 98 is exposed. When the nebulizer delivery device 11 is a jet nebulizer, the compressed air is stored in the housing. When the on/off switch 98 shown in FIG. 6 is in the "on" position, compressed air flows through the retractable hose 20 into nebulizer chamber 26 as shown in FIG. 2. The compressed air converts the liquid medication solution into a mist that can be inhaled by the child through a mouthpiece 16 or the face mask 54.

Alternatively, when the nebulizer 44 is an ultrasonic nebulizer, sound waves are generated by the housing. When the on/off switch 98 is in the "on" position, sound waves travel through the retractable hose 20 into nebulizer chamber 26 as shown in FIG. 2. The sound waves convert the liquid medication solution into a mist that can be inhaled by the child through the mouthpiece 16 or the face mask 54.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A nebulizer device comprising:
   a) a nebulizer;
   b) a housing having a shape of a toy automotive vehicle for retaining the nebulizer therein including an egress port;
   c) a nebulizer delivery device comprising a mouth piece and face mask for placement over a child's mouth when in use;
   d) a hose connected at a first end to said egress port and at a second end to said nebulizer delivery device for providing a liquid within said nebulizer through said egress port to said nebulizer delivery device for ingestion by a user, said hose being retractable for storage within said vehicle when not in use;
   e) a carrying case having a shape of a garage corresponding to said vehicle for storing said vehicle containing said nebulizer, whereby said mouthpiece, face mask and hose are completely concealed within said vehicle when not in use; and
   f) said vehicle having a hood and a trunk with a lid, said egress port being located under said hood, and said face mask, nebulizer device and hose being stored in said trunk when not in use.

2. The nebulizer as recited in claim 1, wherein said vehicle is a fire engine.

3. The nebulizer as claimed in claim 2, wherein said garage is in the shape of a fire house.

4. The nebulizer as recited in claim 1, wherein said vehicle is an airplane.

5. The device as recited in claim 4, wherein said airplane further includes a nose compartment said hood being a nose door pivotally connected to said airplane for providing selective access to said nose compartment.

6. The nebulizer as claimed in claim 5, wherein said trunk is a cargo compartment and a cargo door pivotally connected to said airplane for providing selective access to said cargo compartment.

7. The nebulizer as claimed in claim 6, wherein said garage is in the shape of an airplane hanger.

8. The nebulizer as recited in claim 1, wherein said vehicle is an ambulance.

9. The nebulizer as claimed in claim 8, wherein said garage is in the shape of a hospital.

10. The nebulizer as recited in claim 1, wherein said carrying case contains a plurality of storage compartments.

11. The nebulizer as recited in claim 1, wherein said carrying case contains a strap for use in carrying said nebulizer.

12. The nebulizer as recited in claim 11, wherein said strap is adjustable.

* * * * *